US008541452B2

(12) United States Patent
Chouinard et al.

(10) Patent No.: US 8,541,452 B2
(45) Date of Patent: Sep. 24, 2013

(54) METHOD FOR TREATING BINGE-EATING DISORDER

(76) Inventors: Guy Chouinard, Montreal (CA); Charles-Siegfried Peretti, Champigny (FR)

(*) Notice: Subject to any disclaimer, the term of this patent is extended or adjusted under 35 U.S.C. 154(b) by 1903 days.

(21) Appl. No.: 11/244,645

(22) Filed: Oct. 6, 2005

(65) Prior Publication Data

US 2007/0082928 A1    Apr. 12, 2007

(51) Int. Cl.
*A61K 31/445* (2006.01)

(52) U.S. Cl.
USPC .......................................................... 514/319

(58) Field of Classification Search
USPC .......................................................... 514/319
See application file for complete search history.

(56) References Cited

U.S. PATENT DOCUMENTS

| | | | |
|---|---|---|---|
| 6,333,357 B1 | 12/2001 | Eig | 514/646 |
| 6,906,081 B2 | 6/2005 | Hey et al. | 514/297 |

FOREIGN PATENT DOCUMENTS

WO    WO03/024450 A1 *  3/2003

OTHER PUBLICATIONS

Tanaka et al. Prediction of psychiatric response to donepezil in patients with mild to moderate Alzheimer's disease. Journal of the Neurological Sciences 225 (2004) pp. 135-141.*
Zhang et al. Cholinergic drugs for Alzheimer's disease enhance in vitro dopamine release. Molecular Pharmacology 66:538-544, 2004. vol. 66, No. 3.*
Cecil Textbook of Medicine, 21 st Edition, 2003, pp. 2051-2052.*
Bruera et al. The effect of donepezil on sedation and other symptoms in patients receiving opioids for cancer pain: a pilot study. Journal of pain and symptom Management vol. 26 No. 5. Nov. 2003 pp. 1049-1054.*
Jane N. Kogan, PhD., Barry A. Edelstein, PhD., and Deborah R. McKee, M.A.: Assessment of Anxiety in Older Adults: Current Status. Journal of Anxiety Disorders, vol. 14, No. 2, pp. 109-132, 2000.
Laura E. Gibbons, Linda Teri, Rebecca G. Logsdon and Susan M. McCurry: Journal of Geriatric Psychiatry and Neurology. J. Geriatr Psychiatry Neurol 2006; 19; 202 _DO1:10.1177/ 0891988706292758.
Claudia Cooper, Cornelius Katona, Martin Orrell, and Gill Livingston: Coping strategies and anxiety in caregivers of people with Alzheimer's disease: The Laser-AD study. Journal of Affective Disorders 90 (2006) 15-20.
Louise Ferretti, Susan M. McCurry, Rebecca Logsdon, Laura Gibbons and Linda Teri: Journal of Geriatric Psychiatry and Neurology. J. Geriatr Psychiatry Neurol 2001; 14; 52 _DOI:10.1177/ 089198870101400111.
Rachel B. Mahoney,Sc, Regan Hons, M.B. Ciaran, Ch.B., MRCPsych, Cornelium Katona, M.D., FRCPsych, Gill Livingston M.D., FRCPsych. Anxiety and Depression in Family Caregivers of People With Alzheimer Disease: The Laser-AD Study. American Journal of Geriatric Psychiatry, Issue: vol. 13(9), Sep. 2005, p.795-801.
Jeffrey L. Cummings, MD; The Neuropsychiatric Inventory: Assessing psychopathology in dementia patients; Neurology 1997;48(Suppl 6):S10-S16.
William J. Burke; William H. Roccaforte, M.D.; Steven P. Wengel, M.D. American Journal of Psychiatry, Jul. 1999; 156(7); 1117a-1118.

* cited by examiner

*Primary Examiner* — Jennifer M Kim
(74) *Attorney, Agent, or Firm* — Vidas, Arrett & Steinkraus, P.A.

(57) ABSTRACT

A method for treating anxiety disorders and other disorders using cholinesterase inhibitors including donepezil and its pharmaceutically acceptable salts.

1 Claim, No Drawings

METHOD FOR TREATING BINGE-EATING DISORDER

CROSS-REFERENCE TO RELATED APPLICATIONS

None.

STATEMENT REGARDING FEDERALLY SPONSORED RESEARCH OR DEVELOPMENT

Not Applicable.

BACKGROUND OF THE INVENTION

1. Field of the Invention

This invention relates to treatment of Anxiety Disorders including Post Traumatic Stress Disorder (PTSD), Acute Stress Disorder (ASD), Generalized Anxiety Disorder (GAD), Substance Abuse/Dependence (SA/D), Insomnia, Binge-Eating Disorder (BED) and Gamma hydroxybutyrate (GHB) drug-induced flashbacks including all of the traumatic stress disorders, military or non-military, rape and sexual abuse, drug induced or not, in humans including children by administration of donepezil hydrochloride, its derivatives and pharmaceutically acceptable salts.

2. Description of the Related Art

Donepezil is a generic term to identify the chemical compound (±)-2,3-dihydro-5,6-dimethoxy-2-[[1-(phenylmethyl)-4-piperidinyl]methyl]-1H-inden-1-one hydrochloride. It is useful in the therapy of Alzheimer's disease and its mild and severe forms. It belongs to acetylcholinesterase inhibitors with a dual histamine H3 receptor antagonist/M2 muscarinic antagonist, which includes donepezil, heptylphysostigmine, tacrine, rivastigmine and galantamine. Also in Alzheimer's disease, antagonists of the N-methyl-D-aspartate (NMDA) receptors like memantine are prescribed. It also includes a combination of a histamine H3 receptor antagonist and an M2 muscarinic antagonist which could be given with an acetylcholinesterase inhibitor.

The art described in this section is not intended to constitute an admission that any patent, publication or other information referred to herein is "prior art" with respect to this invention, unless specifically designated as such. In addition, this section should not be construed to mean that a search has been made or that no other pertinent information as defined in 37 C.F.R. §1.56(a) exists.

BRIEF SUMMARY OF THE INVENTION

It has been found that donepezil surprisingly has properties that also enable it to be used effectively to treat acute, chronic and delayed PTSD stress symptoms and ASD symptoms, GAD, SA/D including cannabis dependence, insomnia, binge-eating symptoms, GHB and its derivatives, repetitive flashbacks and all of the symptoms derived from PTSD such as anxiety, depression, derealization and depersonalization. The etiology of PTSD, ASD, GAD, SA/D and BED is unknown and the biochemical defect is also unknown.

We postulate that the specific effect of donepezil on PTSD, ASD, GAD, SA/D, BED and all of the other post-traumatic disorders milder forms, whether drug induced or not, implicates an indirect involvement of brain acetylcholine and a dual H3/M2 receptor antagonist in its mechanism of action, as in the treatment of Alzheimer's disease. We propose that the increase of brain acetylcholine and the dual H3/M2 receptor antagonism resulting from the inhibition of acetylcholinesterase and the dual H3/M2 receptor antagonism improves anxiety, insomnia, depression, flashbacks, drug tolerance, drug withdrawal and mood disorders consecutive to post-traumatic stress symptoms to substance dependence and binge-eating symptoms and improves motor coordination, reduces euphoria, lead to improvement in sensation of slowed time, judgement deficit, social withdrawal, recurrent inappropriate compensatory behavior. The immediate effect of stimulation of the GABA B receptors by GHB is not long lasting and is not involved in the present mechanism of action of donepezil in PTSD and ASD. GHB produces a deregulation in Gamma-amino-butyric-acid (GABA), dopamine and opiates function in the brain.

We postulate that donepezil, by inhibition of the brain acetylcholinesterase, corrects the decrease of acetylcholine produced by GHB through the inhibition of the release of dopamine. The standard treatment in PTSD, BED and GAD has been SSRIs including sertraline, fluoxetine, paroxetine and others. The present invention is not related to the official and recommended treatment of PTSD, BED and GAD, it has never been suggested or proposed previously.

Improving cholinergic function and consequently dopamine metabolism will permit the treatment and the recovery from repetitive traumatic or unwanted automatic flashbacks, and SA/D for which there are no well known accepted standard drug treatments.

DETAILED DESCRIPTION OF THE INVENTION

PTSD and ASD, GAD, SA/D, BED are described succinctly in the *American Psychiatric Association Diagnostic and Statistical Manual*, 4th edition, DSM IV, the disclosure of which is incorporated herein by reference.

The anxiety stress disorders have been divided into two major clinical entities: PTSD and ASD (DSM IV). PTSD occurs following three different symptom durations: acute when less than 3 months, chronic when the symptoms last more than 3 months and delayed when the symptoms appear after at least 6 months following the traumatic event. ASD occurs when the symptom last a minimum of 2 days and a maximum of 4 weeks, and start within 4 weeks of the traumatic event. The DSM IV diagnostic criteria for PTSD and ASD can be summarized as follows: the traumatic event has to be life threatening for the individual and for others and their physical integrity has been threatened. This event has been associated with intense fear or terror or feelings of helplessness. The anxiety is associated with three or more of the following symptoms: derealization, depersonalization, absence of emotional response, and reduction in awareness of surroundings. In addition, the presence of flashbacks or reminiscence of the traumatic scene, persistence of the avoidance of the stimuli related to the memory of the traumatic event, presence of anxiety symptoms, distress feeling or impairment of social functioning is observed.

PTSD and ASD can be also part of other psychiatric disorders and is considered secondary to a primary psychopathology such as major depression, other anxiety disorders, and substance abuse disorders. PTSD can also coexist with another psychiatric disorder. The other anxiety disorder included here is Generalized Anxiety Disorder (GAD) which is characterized by excessive anxiety and worry associated or expressed through symptoms that can affect almost all anatomic body regions. The DSM IV has included six associated symptoms to anxiety and worry. SA/D is characterized by a maladaptive behavior, leading to substance abuse manifested by recurrent substance use resulting in significant impairment or distress as defined by DSM IV. Substance dependence is present when the symptoms have never met the criteria for Substance Dependence. BED is characterized by recurrent episodes of binge eating in the absence of the regular use of inappropriate compensatory behaviors characteristic of Bulimia nervosa.

Based on our research, it is apparent that donepezil may be used to safely treat all of these illnesses, and also to treat minor or transient anxiety symptoms and insomnia that do not fulfil diagnostic criteria for which a patient may seek medications from a physician or for which a patient may seek medications over the counter.

We propose donepezil and all related dual H3/M2 receptor antagonist drugs inhibiting acetylcholinesterase and NMDA antagonists, to treat PTSD including rape victims, any sexual abuse, drug-induced or not, any traumatic event associated with anxiety and depressive symptoms, derealization and depersonalization, and flashbacks associated with traumatic event. Anxiety and depressive symptoms associated with PTSD or ASD will be improved by this treatment modality. We propose donepezil and all related drugs to treat GAD and all similar minor forms of anxiety and insomnia disorders which do not necessarily fulfil the DSM IV criteria. We propose donepezil to treat SA/D and all minor forms of maladaptive pattern of substance use by reducing drug craving and drug seeking behavior Case History 1

Miss A is a 23 year-old woman, who consulted at the Department of Psychiatry at Hospital Saint-Antoine in Paris for treatment of psychological sequelae of a rape, which occurred on Jun. 15, 2005 in New York City (NYC). Psychiatric history consisted of one episode of major depressive disorder (MDD) for a 4-month duration in 2004, which was treated with bi-weekly psychotherapy during 6 months, with complete recovery. Miss A has two brothers, aged 33 and 31, and one 28 year-old sister without any psychiatric disorders. Her 53 year-old mother is described as depressive and her 56 year-old father has no psychiatric antecedent.

Miss A had been living in NYC for her work since January 2005. On Jun. 15, 2005, she met some friends after dinner and went dancing with them. She experienced a strange sensation late in the evening after drinking a glass of champagne. She remembered feeling drowsy and confused. She had to stop dancing because of a severe sedation and took a taxi. A man she didn't know until now accompanied her to her apartment, which was unusual for her.

She didn't remember anything about the taxi drive and her trip back home. She remembered being with an unknown man and strangely being led down on her couch in her living room and looking at him.

Thereafter she repeatedly saw herself waking up in the morning and looking at her bed where she had discovered a preservative, a proof that a sexual behaviour had occurred between 2 and 6 am.

She experienced terrifying nightmares and repetitive uncontrolled behaviour consisting of looking at herself waking up alone with a desperate feeling of being sexually abused and of loneliness. Since that day Miss A had been depressed, anxious with severe insomnia and nightmares, and had flashbacks of several events of the dramatic night. About the evening and the rape she remembered only her inability to move, refusing sexual advances of the unknown man, and feeling uncomfortable because of her unusual behaviour.

On Jun. 20, 2005, she consulted in the Department of Psychiatry at Saint-Antoine Hospital in Paris. A diagnosis of post-traumatic stress disorder (PTSD) according to DSM IV was made and Miss A was suspected to have been a victim of Gamma Hydroxybutyrate intake leading to sexual abuse. A legal procedure was initiated in NYC before coming back to Paris. At the time of the event, she was not drunk as the alcohol blood sampling analyses during the legal procedure the morning after the event had shown it (0.05 g/l). A toxicological analysis was performed using hair sample for detection of the suspected drug GHB.

During the initial interview, she was unable to give any detail about the evening and the night of the rape. Miss A requested a method to decrease her anxiety symptoms, insomnia and nightmares associated with the traumatic event. After a discussion about the case, it was decided on Jun. 20, 2005 to initiate donepezil (Aricept(®) 5 mg once a day for 2 weeks. Donepezil was started on Jun. 20, 2005. After one week of treatment, on June 27, the patient said that she began to feel less anxious and to describe some of the details she was unable to give during the first consultation on June 20. She slept better without nightmares and provided, after the 7 days of medication intake, some of the details of the post-traumatic event. She described without anxiety the unknown man's face, some moments of the taxi drive and the time spent in her apartment's elevator. Donepezil dosage was increased to 5 mg b.i.d. on June 27. Two weeks later, on July 11, Miss A was no more anxious nor tense and able to give additional details about the sensation of being forced to kiss the unknown man during the taxi drive and in her apartment's elevator with a feeling of a dirty tongue penetrating her month. Sleep returned to normal without nightmares. Other symptoms, depression and flashbacks also improved.

Case History 2

Miss B is a 33 year-old woman, who consulted one year ago (September 2004) at the Department of Psychiatry at Hospital Saint-Antoine in Paris for treatment of anxiety and depressive symptoms associated with a history of major depression, Generalized Anxiety (GAD), PTSD and cannabis dependence. She was tobacco and alcohol dependent and also had a binge-eating disorder. She had been treated for alcohol dependency several months with acamprosate 333 mg tablets six times a day, which she discontinued one month after her initial visit at Saint-Antoine Hospital. Miss B has no other psychiatric antecedent. She was treated for a 12-month duration MDD, in 2004 and 2005, with mirtazapine 15 mg h.s. and biweekly psychotherapy, which led to a complete recovery of depressive symptoms after 2 months of treatment. Her 55 year-old mother has an Obsessive Compulsive Disorder for which she has been treated with fluoxetine for the last ten years and social phobia. Her father died at the age of 45 from a liver cancer associated with an alcoholic cirrhosis. Miss B has no siblings.

Miss B is a saleswoman in a flower shop and is also an artist painter. She was selected for an antidepressant drug study on May 31, 2005, however she was excluded because cannabis was found in her urine screen. Despite her on-going biweekly psychotherapy, she continued to abuse cannabis at about 2 to 3 joints a day. She also drank about one liter of wine a day, which she decreased slightly to half a liter a day about six weeks before starting treatment with donepezil. Because of the persistence of her anxiety symptoms associated with GAD and of her complaints of flashbacks associated with her cannabis intake, we decided to prescribe donepezil 5 mg once a day on Aug. 25, 2005. After one week of treatment, we observed a significant decrease in flashbacks both in terms of frequency and intensity. The number of flashbacks went down from at least ten severe and intense flashbacks a day to one or two mild intensity flashbacks. She had also complained of nightmares before donepezil treatment which completely disappeared after one week of donepezil treatment. In addition, donepezil significantly produced a decrease in her alcohol intake. This decrease in alcohol intake was not observed during her previous drug treatment for alcohol abuse. Surprisingly, she was able to completely stop cannabis smoking without any withdrawal symptoms, nor craving symptoms.

The most significant effect of donepezil was on her flashbacks. The flashbacks consisted of repeatedly seeing her previous boyfriend beating her up and raping her at the age of 19. She was having these flashbacks at least ten times a day before donepezil treatment and after one week of treatment, the flashbacks nearly disappeared. Furthermore, she reported that her motor coordination improved, she was no longer euphoric, had no more sensations of slowed time, her judgement significantly improved and she was no longer socially withdrawn as she was before donepezil treatment. Her verbal fluency and cognitive performances did not improve. Thus, the improvement in cannabis intoxication and abuse was not related to the effect of donepezil on cognition. In addition, surprisingly, she noticed that her binge-eating disorder, which was present during many years, completely disappeared after one week of donepezil treatment. She was seen for follow-up on Aug. 30 and Sep. 2, 2005. She felt much improved as regarded her GAD anxiety symptoms (nervousness, muscle tension, restlessness, anxiety, worry, insomnia, and tremor). She also reported that her craving for caffeine, nicotine, cannabis and binge-eating was significantly improved to the extent of disappearing. On Sep. 2, 2005, donepezil was increased to 5 mg b.i.d., which lead to further improvement with disappearance of nightmares related to drug withdrawal.

Case history 3

Mr C is a 45 year-old man who consulted on May 23, 2005 in the Department of Psychiatry at Saint-Antoine Hospital for anxiety and depressive symptoms. He was hospitalized and treated with venlafaxine for MDD that began on the first days of May 2005, after leaving a 15-yearjob at the Canadian Embassy in Paris. He had begun his new job as a marketing agent in a low cost airline company prior to his consultation at Saint-Antoine Hospital.

Mr C complained about insomnia, restlessness, tension, headaches, gastric symptoms, upset stomach, dizziness, fatigue, loss of appetite, and libido deficit. Mr C has been married for 13 years. His wife is a 38 year-old woman working as an assistant director. The couple was well functioning, with two children, a 13 year old girl and a 9 year-old boy in good health. Mr C was in good physical health and had no significant medical antecedent. Mr C had no previous psychiatric antecedent, nor any family history of mental disorders. Mr C's father, a retired fisherman, died at 87 without any evidence of psychiatric illness. Mr C's mother, a housewife, died at 84 from cardiovascular disease. Mr C is the youngest of 14 brothers and sisters.

Mr C was hospitalized in the Department of Psychiatry at Saint-Antoine Hospital and treated for MDD with venlafaxine from Jul. 15 to Aug. 8, 2005, and recovered completely from his depression but his anxiety symptoms persisted at the end of the hospitalisation. His anxiety consisted of excessive worrying, restlessness, tension, fatigue, loss of concentration, irritability, severe muscle tension and difficulty falling asleep. These symptoms met the GAD DSM IV criteria and persisted during the depressive episode and also when he no longer met the criteria for MDD. He was not able to return to work because of his anxiety symptoms which did not respond to the ongoing venlafaxine treatment 100 mg t.i.d. We decided to prescribe donepezil 5 mg once a day on Sep. 9, 2005 to treat his anxiety symptoms. No side effects were observed on Sep. 16, 2005 after one week of treatment, but a definite anti-anxiety effect of donepezil was noted, and it was decided to increase the dosage to 5 mg b.i.d. in order to further improve the anti-anxiety effect. On Sep. 22, 2005, 6 days after increasing donepezil, Mr C was able to return to work without any anxious symptoms, and his complete recovery was clearly related to donepezil intake and increased dosage.

Dosages

The usual dosage levels may vary depending upon the patient. However, treatment of the various psychiatric symptoms and disorders mentioned here will usually entail administering between 5 mg/day to 10 mg/day of donepezil, which may be given in any vehicle under which the drug is formulated, including orally. The preferred range may be between 5 mg/day to 10 mg/day. The therapeutic benefit of controlling flashbacks and related distress, mood variations and anxiety, primary or secondary insomnia with nightmares that was seen indicates that a dosage of from about 5 mg to about 10 mg/day may provide good results to such patients. The drug appears ideal for the adults with anxiety, insomnia, nightmares, substance abuse, binge eating, PTSD and stress symptoms.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

This completes the description of the preferred and alternate embodiments of the invention. Those skilled in the art may recognize other equivalents to the specific embodiment described herein which equivalents are intended to be encompassed by the claims attached hereto.

The invention claimed is:

1. A method for treating or controlling binge-eating disorder which comprises administering to a non-Alzheimer's patient in need of such treating or controlling an effective amount of donepezil or a pharmaceutically acceptable salt thereof.

* * * * *